US009271712B2

(12) United States Patent
    Kim (10) Patent No.: US 9,271,712 B2
(45) Date of Patent: Mar. 1, 2016

(54) RETRACTION DEVICE FOR LAPAROSCOPY (71) Applicants: Jae-Hwang Kim, Daegu (KR); DALIM CORPORATION, Seoul (KR)

(72) Inventor: Jae-Hwang Kim, Daegu (KR)

(73) Assignees: Jae-Hwang Kim, Daegu (KR); DALIM CORPORATION, Seoul (KR)

( * ) Notice: Subject to any disclaimer, the term of this patent is extended or adjusted under 35 U.S.C. 154(b) by 0 days.

(21) Appl. No.: 14/659,473

(22) Filed: Mar. 16, 2015

(65) Prior Publication Data
    US 2015/0230788 A1    Aug. 20, 2015

Related U.S. Application Data

(62) Division of application No. 13/158,938, filed on Jun. 13, 2011, now Pat. No. 8,979,746.

(51) Int. Cl.
    *A61B 17/02*    (2006.01)
    *A61B 17/04*    (2006.01)
    *A61B 17/28*    (2006.01)
    *A61B 17/00*    (2006.01)

(52) U.S. Cl.
    CPC ......... *A61B 17/0218* (2013.01); *A61B 17/0487* (2013.01); *A61B 17/28* (2013.01); *A61B 17/2812* (2013.01); *A61B 2017/00349* (2013.01); *A61B 2017/0454* (2013.01)

(58) Field of Classification Search
    CPC ........... A61B 17/0218; A61B 17/0487; A61B 17/28; A61B 17/2812; A61B 2017/00349; A61B 2017/0454
    See application file for complete search history.

(56) References Cited

U.S. PATENT DOCUMENTS

| 5,312,422 A | 5/1994 | Trott |
| 5,337,736 A * | 8/1994 | Reddy ............................ 600/217 |
| 5,776,150 A * | 7/1998 | Nolan et al. .................. 606/148 |
| 2002/0111534 A1* | 8/2002 | Suzuki et al. ................. 600/102 |
| 2011/0082347 A1* | 4/2011 | Okoniewski .................. 600/227 |
| 2013/0066155 A1* | 3/2013 | Keating et al. ................ 600/204 |

FOREIGN PATENT DOCUMENTS

| KR | 10-2011-0120767 A | 11/2011 |
| WO | 2011/022787 A1 | 3/2011 |

* cited by examiner

*Primary Examiner* — Nicholas Plionis
(74) *Attorney, Agent, or Firm* — Novick, Kim & Lee, PLLC; Jae Youn Kim (57) ABSTRACT

Disclosed herein is a retraction device for laparoscopy in which a trocar needle including latching grooves formed at the side of the lower end thereof is inserted into a trocar tube, both ends of which are opened, to form a laparoscopic platform, the laparoscopic platform pierces an abdominal wall and the trocar needle is pushed into an abdominal cavity so that the latching grooves are exposed to the outside of the trocar tube, sutures connected to tissue retractors retracting tissues are hung on the latching grooves, and then the trocar needle of the laparoscopic platform is drawn upwards so that the latching grooves are inserted back into the trocar tube to fix the tissue retractors to the laparoscopic platform. The retraction device for laparoscopy prevents the tissues from being unnecessarily damaged due to retraction and facilitates convenient retraction of the tissues without the help of assistant's two hands.

2 Claims, 10 Drawing Sheets

RETRACTION DEVICE FOR LAPAROSCOPY

BACKGROUND OF THE INVENTION

1. Field of the Invention

The present invention relates to a retraction device for laparoscopy which retracts tissues without the help of assistant's hands during laparoscopy.

2. Description of the Related Art

Recently, laparoscopy, which is performed within the abdomen using a subminiature video camera and various surgical tools inserted into the abdomen through plural small incisions of usually 0.5-1.5 cm, is being applied to a wide variety of diseases affecting organs in the abdominal cavity.

Such laparoscopy uses a small incision size as compared to traditional laparotomy, thus having advantages, such as reduced surgical pain, rapid recovery and minimal or no scarring.

The above laparoscopy requires retraction of a tissue so as to assist in surgery. As one example, laparoscopic anterior resection of a patient suffering lesion of the rectum and colon requires retraction of the rectum when dissection of the rectum is performed after dissection of the sigmoid colon.

Dissection of the rectum which is generally performed is achieved by a method in which an assistant draws the intestinal tract or the mesentery with laparoscopic clamps, or binds and draws the rectum with a thin string.

However, such a method requires assistant's one hand or two hands to draw the rectum and thus has a drawback in that the assistant cannot help a main operator. Particularly, when an experienced doctor grants a right as a main operator to a beginning surgeon and the experienced doctor serves as an assistant, drawing of the rectum with assistant's two hands may cause a dangerous situation.

As another example, laparoscopic low anterior resection of a female patient suffering rectal cancer requires retraction of the uterus to the abdominal wall. In this case, a method in which a needle connected to a suture is inserted into the abdominal cavity through the abdominal wall from the outside, passes through the uterus, exits the abdominal cavity through the abdominal wall, and is then ligated is mainly used.

However, such a method requires penetration of the abdominal wall twice and easily causes tearing of the uterus due to the pressure of the suture, thereby increasing a possibility of uterine hemorrhage.

Therefore, a retraction device which facilitates convenient retraction of tissues without damage to the tissues and frees assistant's two hands during surgery so as to enable the assistant to more actively assist in surgery is necessary.

SUMMARY OF THE INVENTION

Therefore, the present invention has been made in view of the above problems, and it is an object of the present invention to provide a retraction device which prevents tissues from being unnecessarily damaged due to retraction, facilitates convenient retraction of the tissues without the help of assistant's two hands, enables an assistant to more actively assist in surgery, and assures a wide field of surgical vision.

In accordance with an aspect of the present invention, the above and other objects can be accomplished by the provision of a retraction device for laparoscopy in which a trocar needle including latching grooves formed at the side of the lower end thereof is inserted into a trocar tube, both ends of which are opened, to form a laparoscopic platform, the laparoscopic platform pierces an abdominal wall and the trocar needle is pushed into an abdominal cavity so that the latching grooves are exposed to the outside of the trocar tube, sutures connected to tissue retractors retracting tissues are hung on the latching grooves, and then the trocar needle of the laparoscopic platform is drawn upwards so that the latching grooves are inserted back into the trocar tube to fix the tissue retractors to the laparoscopic platform.

In accordance with another aspect of the present invention, there is provided a retraction device for laparoscopy in which a pair of clamps provided with interface surfaces having prominence and depression shapes corresponding to each other is formed at left and right forceps parts to form fixing forceps, a tap is attached to the end of a suture provided with a needle to form a tap type retractor, the needle of the tap type retractor penetrates one side of a tissue so that the tap is supported by the outer wall of the tissue, the needle having penetrated the tissue passes through an abdominal wall and exits an abdominal cavity, the suture of the tap type retractor is inserted between the interface surfaces of the clamps of the fixing forceps located on the upper surface of the abdominal wall, and then the clamps are moved towards each other to firmly fix the tap type retractor.

In accordance with yet another aspect of the present invention, there is provided a retraction device for laparoscopy in which a pair of clamps provided with interface surfaces having prominence and depression shapes corresponding to each other is formed at left and right forceps parts to form fixing forceps, a toothed part with latching protrusions arranged in a line and an insertion hole into which one of the latching protrusions is inserted are formed at one end and the other end of a band-shaped main body to form a band type retractor, a suture provided with a needle is connected to the frontmost latching protrusion of the toothed part of the band type retractor, the band type retractor surrounds the outer surface of a tissue, one of the latching protrusions is inserted into the insertion hole, and the needle connected to the band type retractor passes through an abdominal wall and exits an abdominal cavity, the suture of the band type retractor is inserted between the interface surfaces of the clamps of the fixing forceps located on the upper surface of the abdominal wall, and then the clamps are moved towards each other to firmly fix the band type retractor.

BRIEF DESCRIPTION OF THE DRAWINGS

The above and other objects, features and other advantages of the present invention will be more clearly understood from the following detailed description taken in conjunction with the accompanying drawings, in which:

FIGS. 5(a) to 7(c) are views illustrating various states of tissues retracted using the retraction device in accordance with the embodiment of the present invention;

FIGS. 9(a) to 9(c) are perspective views illustrating states of a tap type retractor fixed to the fixing forceps in accordance with the embodiment of the present invention;

FIGS. 10(a) to 10(c) are perspective views illustrating states of a band type retractor fixed to the fixing forceps in accordance with the embodiment of the present invention; and FIGS. 11(a) to 11(c) are perspective views illustrating change of the retracting direction of a tissue using the retraction devices in accordance with the embodiments of the present invention.

DETAILED DESCRIPTION OF THE INVENTION

Now, preferred embodiments of the present invention will be described in detail with reference to the annexed drawings.

The present invention provides a retraction device for laparoscopy in which a laparoscopic platform fixed to an abdominal wall is installed within an abdominal cavity or fixing forceps are installed at the outside of the abdominal cavity, a band type retractor or a tap type retractor simply retracts a tissue, and then such a retractor is fixed to the laparoscopic platform or the fixing forceps so as to facilitate convenient retraction of the tissue without the help of assistant's two hands during surgery and minimize unnecessary damage to the tissue during retraction.

Figure 1:
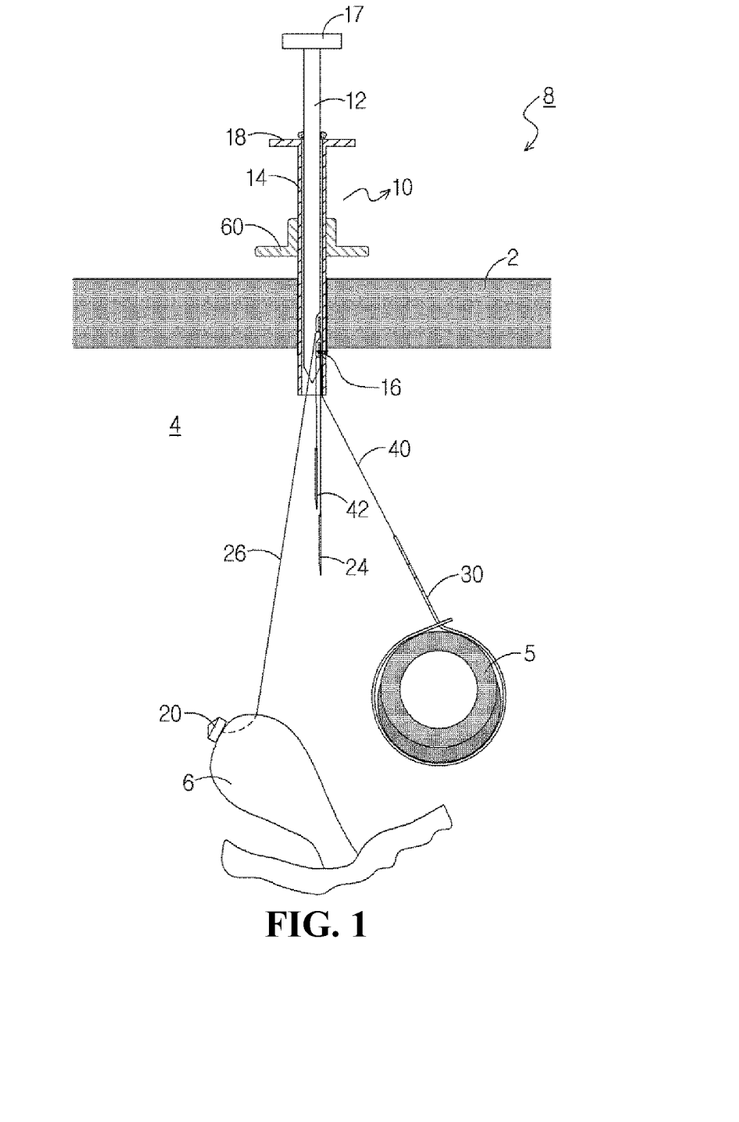
FIG. 1 is a perspective view of a retraction device in accordance with one embodiment of the present invention.
Figure 2:
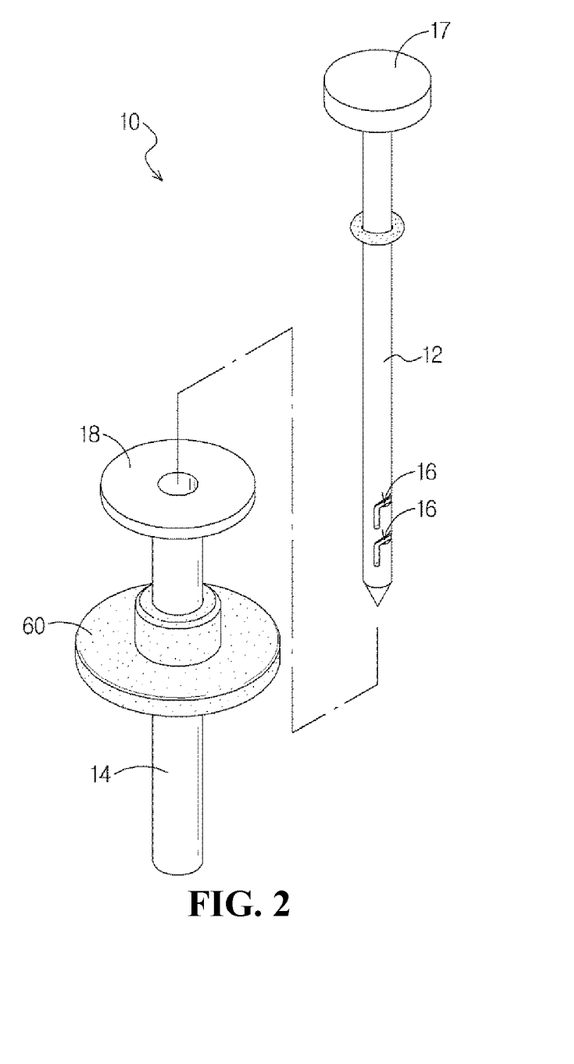
FIG. 2 is a perspective view of a laparoscopic platform in accordance with the embodiment of the present invention.
Figure 3:
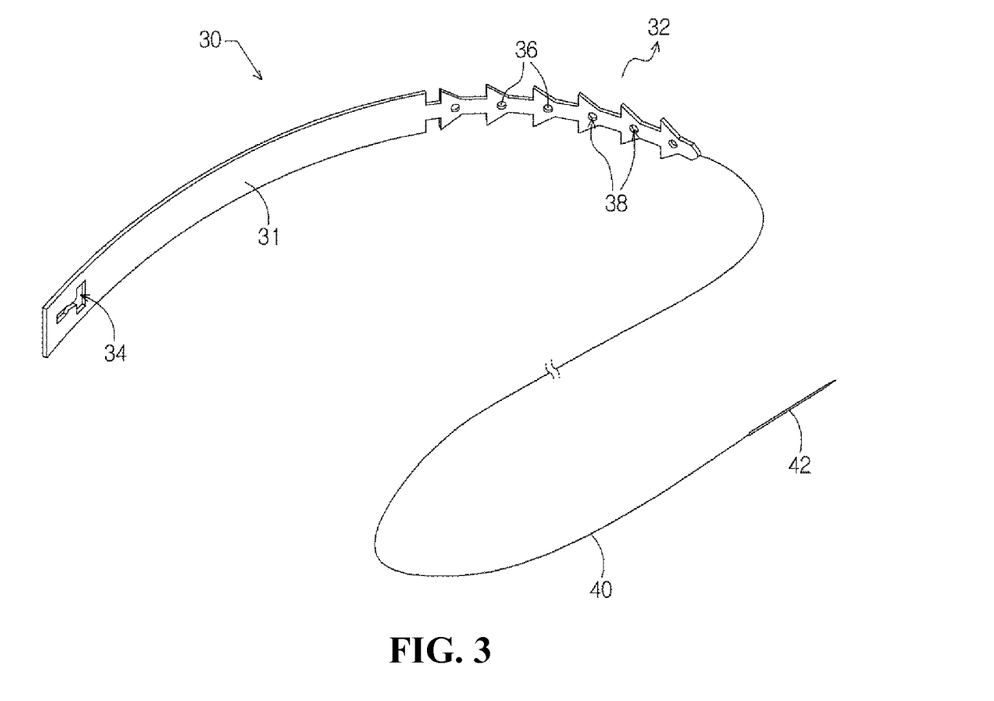
FIG. 3 is a perspective view of a band type retractor in accordance with the embodiment of the present invention.
Figure 4:
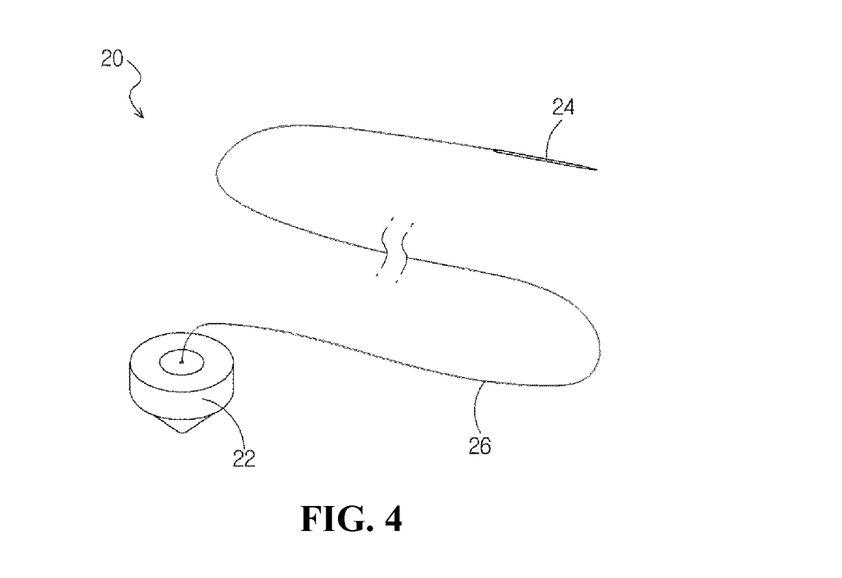
FIG. 4 is a perspective view of a tap type retractor in accordance with the embodiment of the present invention.
Figure 7A:
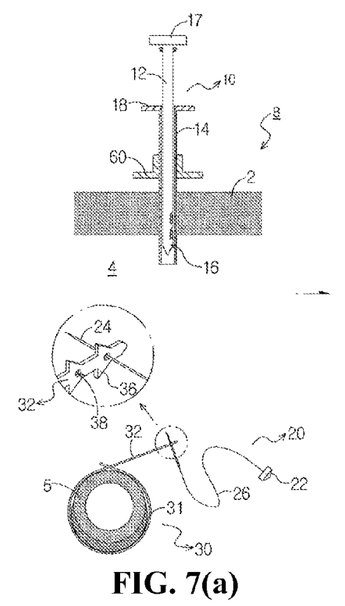
Figure 7B:
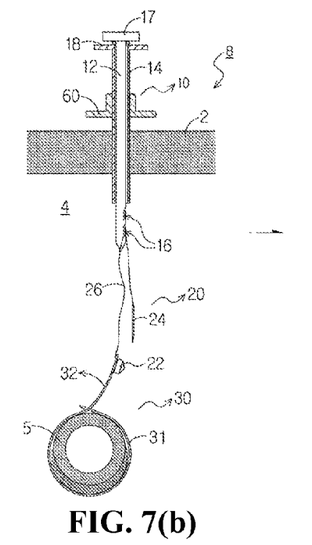
Figure 7C:
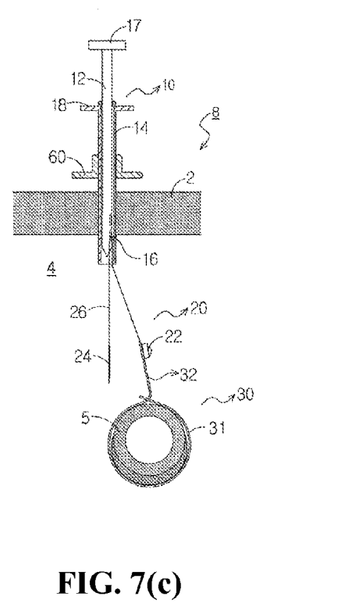
Figure 8A:
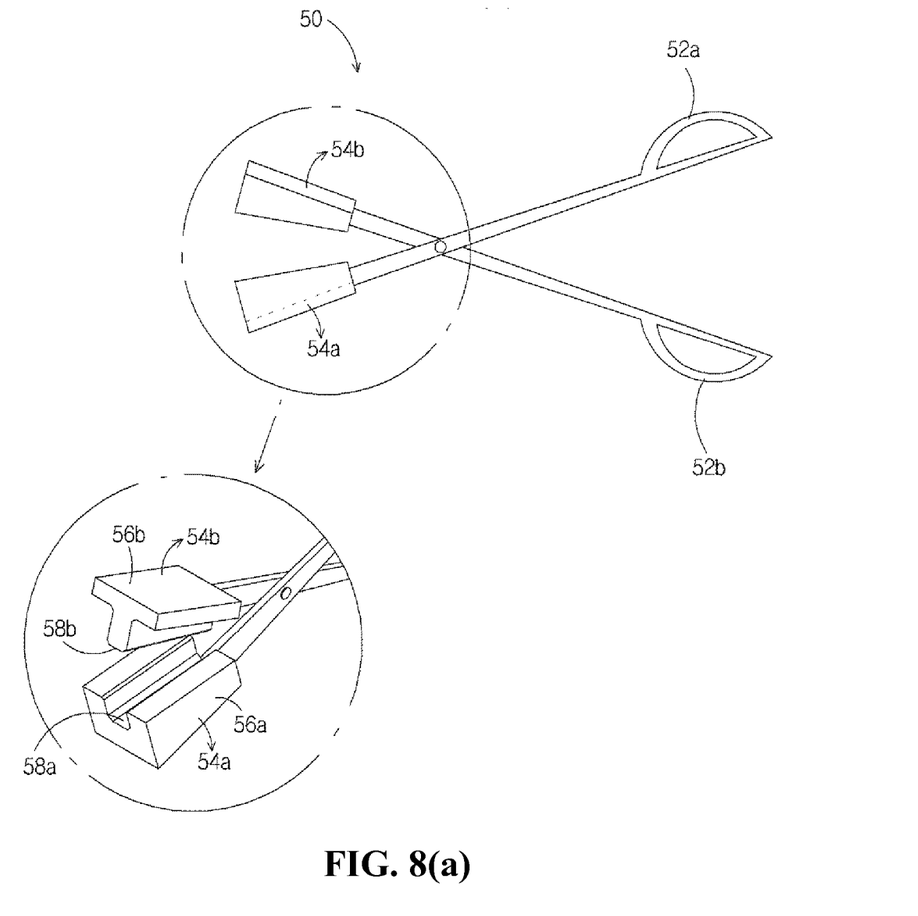
FIGS. 8(a) and 8(b) are perspective views of fixing forceps in accordance with another embodiment of the present invention.
Figure 8B:
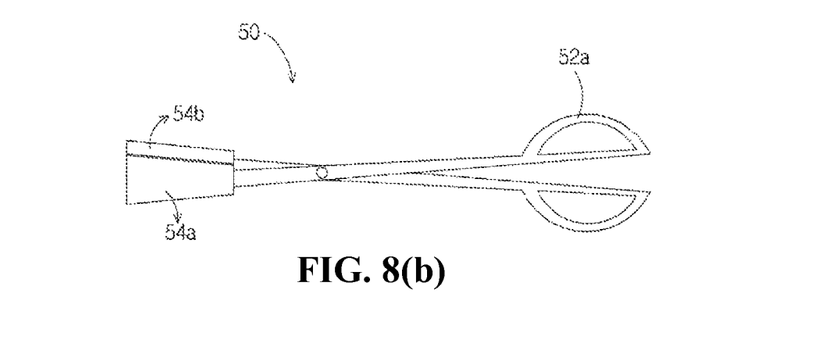
Figure 9A:
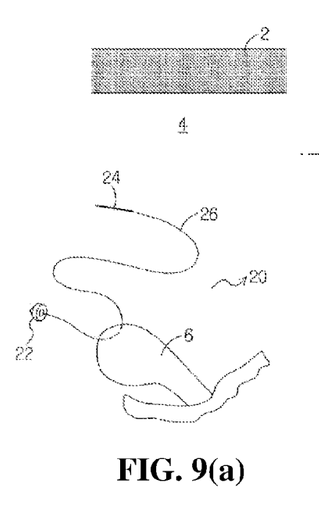
Figure 9B:
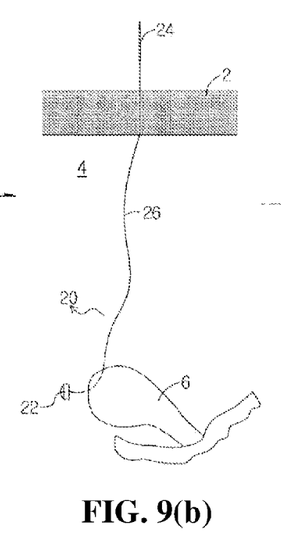
Figure 9C:
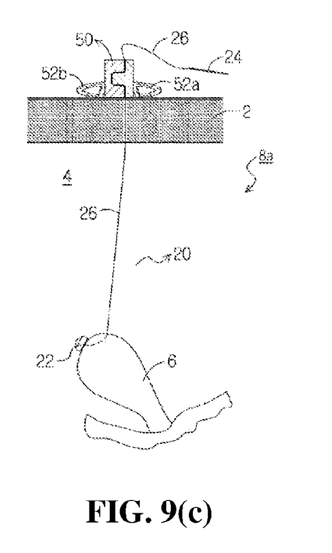
Figure 10A:
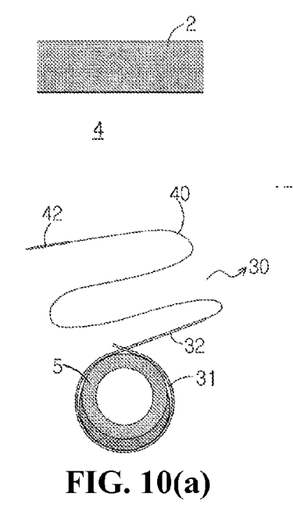
Figure 10B:
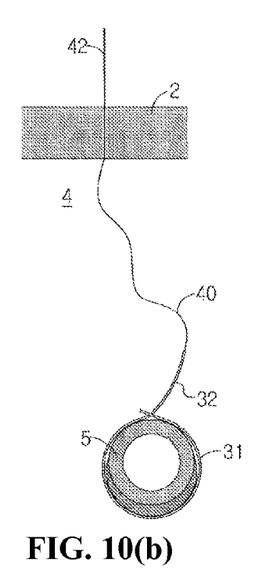
Figure 10C:
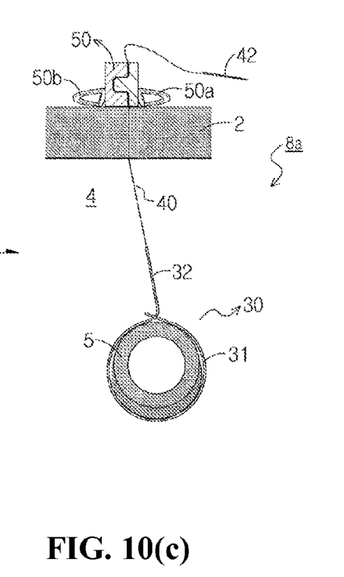
Figure 11A:
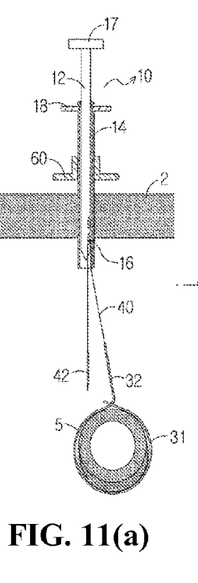
Figure 11B:
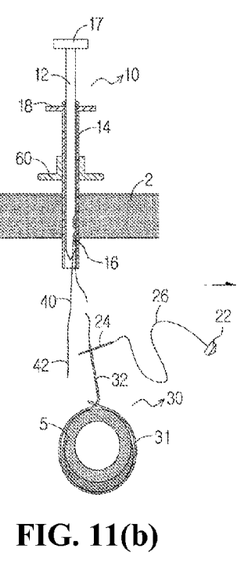
Figure 11C:
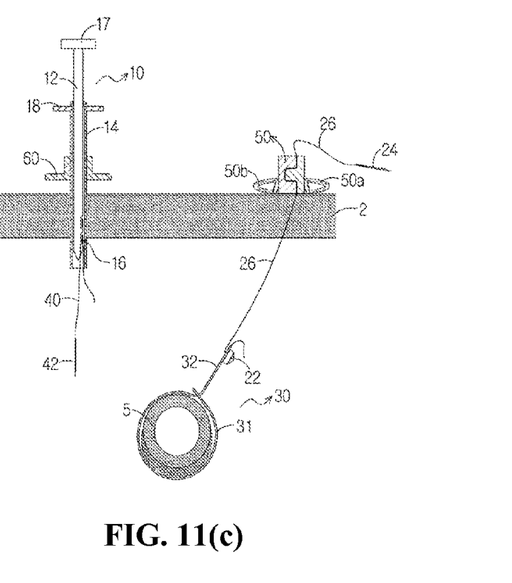

FIG. 1 is a perspective view of a retraction device in accordance with one embodiment of the present invention, FIG. 2 is a perspective view of a laparoscopic platform in accordance with the embodiment of the present invention, FIG. 3 is a perspective view of a band type retractor in accordance with the embodiment of the present invention, FIG. 4 is a perspective view of a tap type retractor in accordance with the embodiment of the present invention, FIGS. 5(a) to 7(c) are views illustrating various states of tissues retracted using the retraction device in accordance with the embodiment of the present invention, FIGS. 8(a) and 8(b) are perspective views of fixing forceps in accordance with another embodiment of the present invention, FIGS. 9(a) to 9(c) are perspective views illustrating states of a tap type retractor fixed to the fixing forceps in accordance with the embodiment of the present invention, FIGS. 10(a) to 10(c) are perspective views illustrating states of a band type retractor fixed to the fixing forceps in accordance with the embodiment of the present invention, and FIGS. 11(a) to 11(c) are perspective views illustrating change of the retracting direction of a tissue using the retraction devices in accordance with the embodiments of the present invention.

A retraction device 8 for laparoscopy in accordance with one embodiment of the present invention is used to fix tissue retractors 20 and 30 retracting tissues 5 and 6 within an abdominal cavity 4.

The retraction device 8 for laparoscopy in accordance with the embodiment of the present invention shown in FIG. 1 includes a laparoscopic platform 10 penetrating an abdominal wall 2, and the tissue retractors 20 and 30 retracting the tissues 5 and 6 and fixed to the laparoscopic platform 10.

As shown in FIG. 2, the laparoscopic platform 10 in accordance with the embodiment of the present invention is configured such that a trocar needle 12 provided with latching grooves 16 formed thereon is inserted into a trocar tube 14 provided with both opened ends. The tip of the trocar needle 12 of the laparoscopic platform 10 is sharp, and the plural latching grooves 16 are formed on the side wall of the lower end of the trocar needle 12. The trocar needle 12 has a larger length than the trocar tube 14 such that, when the trocar needle 12 is inserted into the trocar tube 14, the latching grooves 16 may protrude from the trocar tube 14. The latching grooves 16 of the trocar needle 12 may be arranged in a line on the side wall of the lower end of the trocar needle 12.

Sutures 26 and 40 connected to the tissue retractors 20 and 30 retracting the tissues 5 and 6 are hung on the latching grooves 16 of the trocar needle 12.

The trocar tube 14 of the laparoscopic platform 10 has a diameter such that the trocar needle 12 may be inserted into the trocar tube 14, and both ends of the trocar tube 10 are opened. The lower end of the trocar tube 14 is level so as not to cause tissue damage.

Head parts 17 and 18 having larger diameters than the body parts of the trocar needle 12 and the trocar tube 14 are respectively formed at the upper ends of the trocar needle 12 and the trocar tube 14. The diameter of the head part 18 of the trocar tube 14 is larger than the diameter of the head part 17 of the trocar needle 12. The head part 18 of the trocar tube 14 supports the head part 17 of the trocar needle 11, thus serving as a latching protrusion of the trocar needle 12. Further, the head part 17 of the trocar needle 12 serves as a handle, thus facilitating pushing or drawing of the trocar needle 12.

After the laparoscopic platform 10 pierces the abdominal wall 2, the trocar needle 12 is pushed into the abdominal cavity 4 so that the latching grooves 16 formed at the lower end of the trocar needle 12 are exposed to the outside of the trocar tube 14, the sutures 26 and 40 of the tissue retractors 20 and 30 retracting the tissues 5 and 6 are respectively hung on the latching grooves 16, and the trocar needle 12 is drawn upwards and inserted back into the trocar tube 14 so that the sutures 26 and 40 are fixed so as not to be easily separated from the latching grooves 16.

Here, the trocar tube 14 located at the outside of the abdominal wall 2 may be fixed by a fixture 60 formed of an elastic material, such as rubber or a synthetic resin. The fixture 60 which is formed in a flange shape surrounds the outer circumferential surface of the trocar tube 14 and prevents the trocar tube 14 from being drawn into the abdominal wall 2. Further, a fixing ring formed of rubber or a synthetic resin is installed on the outer circumferential surface of the trocar needle 12 adjacent to the head part 18 of the trocar tube 14, thus preventing the trocar needle 12 from being drawn into the abdominal wall 2

The tissue retractors 20 and 30 hung on and fixed to the latching grooves 16 of the laparoscopic platform 10 include a tap type retractor 20 in which a tap 22 is attached to the end of the suture 26 provided with a needle 24, and a band type retractor 30 including a toothed part 32 with latching protrusions 36 arranged in a line and an insertion hole 34 into which one of the latching protrusions 36 is inserted. Either the tap type retractor 20 or the band type retractor 30, or both the tap type retractor 20 and the band type retractor 30 may be fixed to the laparoscopic platform 10.

The tap type retractor 20 may be used in, for example, retraction of an uterus 6 to the abdominal wall when laparoscopic low anterior resection of a female patient suffering rectal cancer is performed, and the band type retractor 30 may be used in, for example, retraction of a rectum 50 when dissection of the rectum 5 is performed after dissection of the sigmoid colon in laparoscopic anterior resection of a patient suffering lesion of the rectum 5 and colon.

From among the tissue retractors 20 and 30, the tap type retractor 20 has the tap 22 attached to the end of the suture 26 provided with the needle 24, as shown in FIG. 4. The tap type retractor 20 is configured such that the needle 24 penetrates one side of the tissue 6 and the tap 22 is supported by the outer wall of the tissue 6 so as to retract the tissue 6. The tap 22 attached to the tap type retractor 20 serves to widely disperse pressure of the suture 26 applied to the tissue 6 and thus to prevent the tissue 6 from being damaged.

The tap 22 preferably has a generally circular shape so as not to damage the tissue 6, and the surface of the tap 22 supported by the outer wall of the tissue 6 is preferably flat so as to widely support the tissue 6 to the maximum extent possible. Further, the tap 22 may be formed of a soft material, such as elastic rubber, silicon or plastic.

In the embodiment of the present invention, the surface of the tap 22 supported by the outer wall of the tissue 6 has a circular shape, and a hemostatic agent can be applied to the surface of the tap 22 so as to reduce hemorrhage due to damage to the tissue 6.

From among the tissue retractors 20 and 30, the band type retractor 30 is formed in a flexible band shape and is rolled up so as to surround the outer surface of the tissue 5, as shown in FIG. 3. In this case, a main body 31 of the band type retractor 30 preferably maintains a round-shaped bending band shape at all times.

The toothed part 32 with the latching protrusions 36 is formed at one end of the bending band-shaped main body 31, and the insertion hole 34 into which one of the latching protrusions 36 is inserted is formed at the other end of the bending band-shaped main body 31.

The toothed part 32 formed at one end of the main body 31 of the band type retractor 30 is provided with the latching protrusions 36 having a rectangular shape, which are arranged in a line. The frontmost latching protrusion 36 of the toothed part 32 has a protruding end, and the suture 40 provided with the needle 42 may be connected to the protruding end of the frontmost latching protrusion 36.

Instead of the suture 40 provided with the needle 42, the tap type retractor 20 may be connected to the band type retractor 30. Connection holes 38 to which the tap type retractor 20 is connected are respectively formed on the latching protrusions 36 of the band type retractor 30. The connection holes 38 of the latching protrusions 36 have a sufficient size to pass the needle 42 and the suture 40 of the tap type retractor 20. The tap type retractor 20 is connected to the band type retractor 30 by allowing the needle 24 of the tap type retractor 20 to pass through the connection hole 38 of one latching protrusion 36 and then the tap 22 to be supported by the outer surface of the latching protrusion 36.

The insertion hole 34 formed at the other end of the main body 31 of the band type retractor 30 has a T shape so that one of the rectangular latching protrusions 36 of the toothed part 32 is inserted into the insertion hole 34.

Now, with reference to FIGS. 5(a) to 7(c), an operating process of the retraction device 8 for laparoscopy in accordance with the embodiment of the present invention will be described.

Figure 5A:
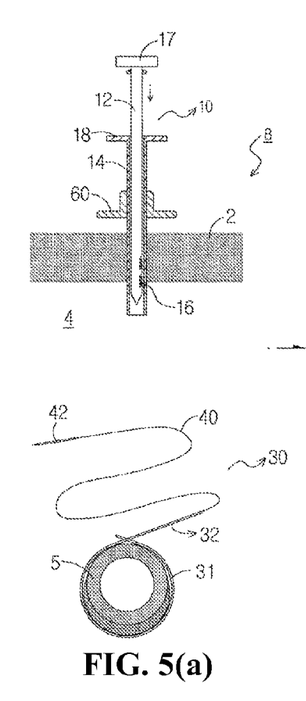
Figure 5B:
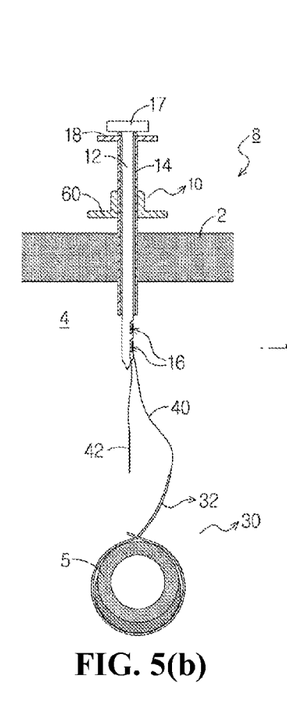

First, a user inserts the laparoscopic platform 10 into the abdominal wall 2 so that one end of the laparoscopic platform 10 is introduced into the abdominal cavity 4. Then, the user pushes the trocar needle 12 into the abdominal cavity 4 using the head part 17 so that the latching grooves 16 are exposed to the outside of the trocar tube 14.

Figure 6A:
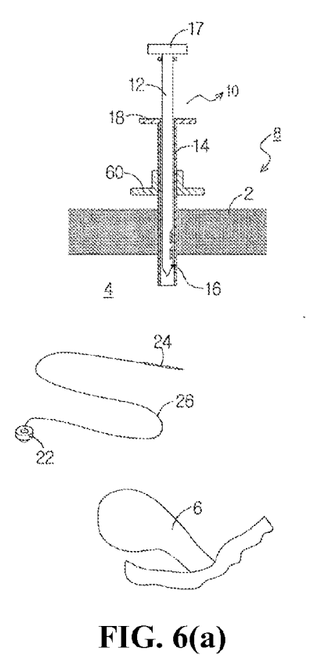
Figure 6B:
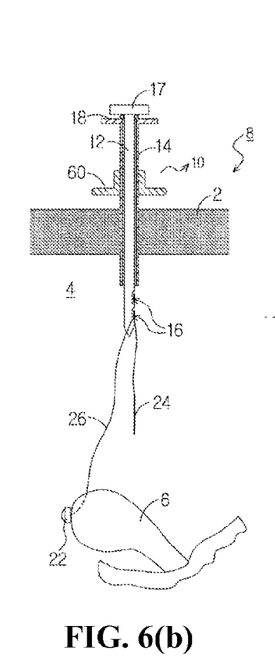
Figure 6C:
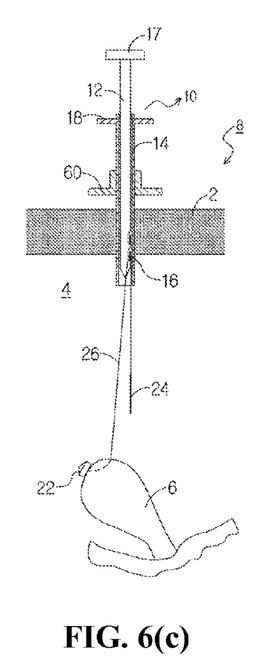

Thereafter, as shown in FIGS. 6(a) to 6(c), the needle 24 of the tap type retractor 20 penetrates one side of the tissue 6, such as the uterus, so that the tap 22 is supported by the outer wall of the tissue 6, and the needle 24 having penetrated the tissue 6 passes through one latching groove 16 of the trocar needle 12 so that the suture 26 of the tap type retractor 20 is hung on the latching groove 16 of the laparoscopic platform 10.

Figure 5C:
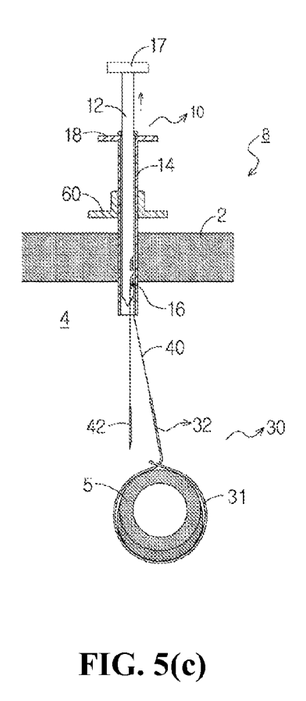

Further, as shown in FIGS. 5(a) to 5(c), after the band type retractor 30 surrounds the outer surface of the tissue 5, such as the rectum, one of the latching protrusions 36 is inserted into the insertion hole 34, and the needle 42 connected to the band type retractor 30 passes through one latching groove 16 of the trocar needle 12 so that the suture 40 connected to the band type retractor 30 is hung on the latching groove 16.

In this case, instead of the suture 40 provided with the needle 42, the tap type retractor 20 may be connected to the band type retractor 30. If the tap type retractor 20 is connected to the band type retractor 30, as shown in FIGS. 7(a) to 7(c), the band type retractor 30 surrounds the outer surface of the tissue 5 and then one of the latching protrusions 36 is inserted into the insertion hole 34. Then, the needle 24 of the tap type retractor 20 passes through the connection hole 38 of one latching protrusion 36 and the suture 26 is drawn so that the tap 22 is supported by the outer surface of the latching protrusion 36. Thereafter, the needle 24 of the tap type retractor 20 connected to the band type retractor 30 is hung on one latching groove 16 of the laparoscopic platform 10.

After the sutures 26 and 40 of the above-described tissue retractors 20 and 30 are hung on the latching grooves 16 of the laparoscopic platform 10, the user draws the head part 17 of the trocar needle 12 of the laparoscopic platform 10 upwards so that the trocar needle 12 is inserted back into the trocar tube 14. Here, in order to prevent downward movement of the trocar needle 12, a fixing ring or a fixing clip provided with an insertion hole, one side part of which is opened, may be inserted between the head part 17 of the trocar needle 12 and the head part 18 of the trocar tube 14 so as to fix the trocar needle 12.

By means of the insertion of the trocar needle 12 of the laparoscopic platform 10 back into the trocar tube 14, the tissue retractors 20 and 30 may be firmly fixed to the laparoscopic platform 10 so as not to separate the sutures 26 and 40 connected to the tissue retractors 20 and 30 from the latching grooves 16.

Hereinafter, a retraction device 8a for laparoscopy in accordance with another embodiment of the present invention will be described. Some parts of the retraction device 8a for laparoscopy in accordance with this embodiment are substantially the same as those of the retraction device 8 for laparoscopy in accordance with the earlier embodiment, and a detailed description thereof will thus be omitted because it is considered to be unnecessary.

The retraction device 8a for laparoscopy in accordance with this embodiment of the present invention may be used to fix tissue retractors 20 and 30 retracting tissues 5 and 6 at the outside of an abdominal cavity 4.

The retraction device 8a for laparoscopy in accordance with this embodiment of the present invention, as shown in FIGS. 9(a) to 10(c), includes fixing forceps 50 including left and right forceps parts 54a and 54b to which a pair of clamps 56a and 56b is attached, and the tissue retractors 20 and 30 retracting the tissues 5 and 6 and configured such that sutures 26 and 40 are clamped by the fixing forceps 50.

The fixing forceps 50 installed at the outside of an abdominal wall 2, as shown in FIGS. 8(a) to 8(c), include the left and right forceps parts 54a and 54b provided with the pair of clamps 56a and 56b formed at the front end of the fixing forceps 50, and left and right handle parts 52a and 52b formed at the rear end of the fixing forceps 50. The fixing forceps 50 are configured such that the clamps 56a and 56b attached to the left and right forceps parts 54a and 54b are moved towards or away from each other using the left and right handle parts 52a and 52b so as to clamp the sutures 26 and 40 of the tissue retractors 20 and 30.

The pair of clamps 56a and 56b attached to the left and right forceps parts 54a and 54b may be rectangular elastic members. For example, the clamps 56a and 56b may be elastic members formed of rubber, silicon or plastic which is harmless to the human body.

Interface surfaces 58a and 58b of the clamps 56a and 56b have prominence and depression shapes corresponding to each other. For example, if one of the interface surfaces 58a and 58b of the pair of clamps 56a and 56b has a depression shape, the other of the interface surfaces 58a and 58b of the pair of clamps 56a and 56b has a prominence shape so as to be engaged with the one of the interface surfaces 58a and 58b.

The interface surfaces 58a and 58b of the pair of clamps 56a and 56b having the prominence and depression shapes serve to firmly clamp the sutures 26 and 40 connected to the tissue retractors 20 and 30.

The tissue retractors 20 and 30 in accordance with this embodiment of the present invention include a tap type retractor 20 in which a tap 22 is attached to the end of the suture 26 provided with a needle 24, and a band type retractor 30 including a toothed part 32 with latching protrusions 36 arranged in a line and an insertion hole 34 into which one of the latching protrusions 36 is inserted.

The band type retractor 30 may be used under the condition that the suture 40 provided with a needle 42 is connected to the frontmost latching protrusion 36 of the toothed part 32 or the tap type retractor 20 is connected to a connection hole 38 of one latching protrusion 36 of the tooted part 32.

Now, with reference to FIGS. 9(a) to 10(c), an operating process of the retraction device 8a for laparoscopy in accordance with this embodiment of the present invention will be described.

In order to retract the tissue 6, such as an uterus, as shown FIGS. 9(a) to 9(c), the needle 24 of the tap type retractor 20 penetrates one side of the tissue 6 so that the tap 22 is supported by the outer wall of the tissue 6, and the needle 24 having penetrated the tissue 6 passes through the abdominal wall 2 and exits the abdominal cavity 4. Then, the suture 26 connected to the needle 24 is inserted between the interface surfaces 58a and 58b of the clamps 56a and 56b of the fixing forceps 50 located on the upper surface of the abdominal wall 2. Thereafter, the clamps 56a and 56b of the left and right forceps parts 54a and 54b are moved towards each other using the left and right handle parts 52a and 52b of the fixing forceps 50, thereby firmly fixing the suture 26 of the tap type retractor 20.

Further, in order to retract the tissue 5, such as a rectum, as shown FIGS. 10(a) to 10(c), after the band type retractor 30 surrounds the outer surface of the tissue 5, one of the latching protrusions 36 is inserted into the insertion hole 34, and the needle 42 connected to the band type retractor 30 passes through the abdominal wall 2 and exits the abdominal cavity 4. Then, the suture 40 connected to the needle 42 is inserted between the interface surfaces 58a and 58b of the clamps 56a and 56b of the fixing forceps 50 located on the upper surface of the abdominal wall 2. Thereafter, the clamps 56a and 56b of the left and right forceps parts 54a and 54b are moved towards each other using the left and right handle parts 52a and 52b of the fixing forceps 50, thereby firmly fixing the suture 40 of the band type retractor 30.

Instead of the suture 40 provided with the needle 42, the tap type retractor 20 may be connected to the band type retractor 30. The band type retractor 30 to which the tap type retractor 20 is connected may be usefully applied when a user desires to change the retracting direction of the tissue 5.

In more detail, when the user desires to change the retracting direction of the tissue 5, as shown in FIGS. 11(a) to 11(c), the suture 40 of the band type retractor 30 fixed to the laparoscopic platform 10 in accordance with one embodiment of the present invention is cut using scissors. Then, the tap type retractor 20 is connected to the band type retractor 20 by allowing the needle 24 of the tap type retractor 20 to pass through the connection hole 38 of one latching protrusion 36 of the band type retractor 30 so that the tap 22 is supported by the latching protrusion 36. Thereafter, the needle 24 of the tap type retractor 20 passes through the abdominal wall 2 in a direction desired by the user, the suture 26 connected to the needle 24 is inserted between the interface surfaces 58a and 58b of the clamps 56a and 56b of the fixing forceps 50 located on the upper surface of the abdominal wall 2, and the clamps 56a and 56b are moved towards each other so as to firmly fix the suture 26.

Through the above-described configurations, the retraction devices 8 and 8a for laparoscopy in accordance with the embodiments of the present invention prevent unnecessary damage to the tissues 5 and 6 due to retraction and simply retract the tissues 5 and 6 without the help of assistant's two hands. Further, the retraction devices 8 and 8a for laparoscopy assure a wide field of surgical vision and enable an assistant to more actively assist in surgery so as to successfully achieve the surgery.

As apparent from the above description, the present invention provides a retraction device which prevents unnecessary damage to tissues due to retraction, such as penetration of the tissues by a needle twice or more, facilitates convenient retraction of the tissues without the help of assistant's two hands, enables an assistant to more actively assist in surgery, and assures a wide field of surgical vision.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A retraction device for laparoscopy, comprising:
a pair of clamps including interface surfaces having prominence and depression shapes corresponding to each other, the pair of clamps being formed at left and right forceps parts to form fixing forceps; and
a tap type retractor including a tap attached to an end of a suture having a needle, the tap having a top flat circular surface configured to support a tissue, a side circumferential surface connected to the top circular surface, and a cone shaped bottom surface connected to the side surface,
wherein the needle of the tap type retractor is configured to penetrate one side of a tissue so that the tap is configured to be supported by an outer wall of the tissue, the needle having penetrated the tissue is configured to pass through an abdominal wall and to exit an abdominal cavity, the suture of the tap type retractor is configured to be inserted between the interface surfaces of the clamps of the fixing forceps being configured to be located on an upper surface of the abdominal wall, and then the clamps are configured to be moved towards each other to firmly fix the tap type retractor.

2. A retraction device for laparoscopy, comprising:
a pair of fixing forceps including a pair of clamps including interface surfaces having prominence and depression shapes corresponding to each other, and left and right forceps parts;
a band type retractor including a band-shaped main body, a toothed part having latching protrusions arranged in a line and disposed at one end of the band-shaped main body, and an insertion hole disposed at another end of the band-shaped main body, wherein the insertion hole is configured to be inserted into one of the latching protrusions; and a suture having a needle and connected to a front latching protrusion of the latching protrusions of the toothed part of the band type retractor, wherein the band type retractor is configured to surround an outer surface of a tissue, the needle connected to the band type retractor is configured to pass through an abdominal wall and to exit an abdominal cavity, the suture of the band type retractor is configured to be inserted between the interface surfaces of the clamps of the fixing forceps being configured to be located on an upper surface of the abdominal wall, and the clamps are configured to be moved towards each other to firmly fix the band type retractor.

* * * * *